United States Patent [19]

Dickoré et al.

[11] 4,052,460
[45] Oct. 4, 1977

[54] PRODUCTION OF 3,3-DIMETHYL-2-OXO-BUTYRIC ACID SALT

[75] Inventors: Karlfried Dickoré, Leverkusen; Hans Dieter Engels, Solingen; Hans Krätzer, Wuppertal; Walter Merz, Leverkusen, all of Germany

[73] Assignee: Bayer Aktiengesellschaft, Leverkusen, Germany

[21] Appl. No.: 650,651

[22] Filed: Jan. 20, 1976

[51] Int. Cl.$^2$ .................... C07C 45/00; C07C 49/16
[52] U.S. Cl. .................... 260/593 H; 260/535 A; 260/526 R
[58] Field of Search .................... 260/593 H

[56] References Cited
PUBLICATIONS

Hill et al., J.A.C.S., vol. 55, pp. 2509–2512 (1933).
Weygand et al., Preparative Organ. Chem., pp. 189–191 (1973).
Dahl et al., Liebigs Ann. Chem., vol. 752, pp. 206–208, (1971).
Aston et al., Organic Synthesis Coll., vol. 3, pp. 538–541.
House, Organic Synthesis, pp. 459–464 (1974).

Primary Examiner—James O. Thomas, Jr.
Assistant Examiner—James H. Reamer
Attorney, Agent, or Firm—Burgess, Dinklage & Sprung

[57] ABSTRACT

Dichloropinacolone is produced by introducing into pinacolone twice the molar amount of chlorine, the exothermic reaction mass being cooled initially to maintain the temperature below about 50° C until about 60 to 80% of the chlorine has been introduced, and then heating the reaction mass to a temperature above 50° C during introducing of the remainder of the chlorine, thereby to produce dichloropinacolone, and terminating chlorine introduction when the dichloropinacolone content of the reaction mass is at least about 97%. The molten product is added to an aqueous solution of an alkali maintained at a temperature of at least about 50° C, the alkali being present in more than three times the molar amount of the dichloropinacolone. To the resulting solution of a salt of 3,3-dimethyl-2-hydroxy-butyric acid, brought to a pH of about 9 to 12, there is added approximately the stoichiometric amount of potassium permanganate. Solid MnO$_2$ precipitates out and is separated from the substantially pure dissolved salt of 3,3-dimethyl-2-oxo-butyric acid. The product is a known compound suited for further syntheses.

2 Claims, No Drawings

PRODUCTION OF 3,3-DIMETHYL-2-OXO-BUTYRIC ACID SALT

The present invention relates to the preparation of a salt of 3,3-dimethyl-2-oxo-butyric acid starting with pinacolone.

3,3-dimethyl-2-oxo-butyric acid is disclosed in application Ser. No. 640,830, filed in the name of Walter Merz on Dec. 15, 1975 now pending, as reacting with thiocarbohydrazide to produce 3-mercapto-4-amino-6-tert.-butyl-1,2,4-triazine-5-one which, upon methylation, yields 3-methylthio-4-amino-6-tert.-butyl-1,2,4-triazine-5-one, which exhibits marked selective herbicidal activity.

It is an object of the present invention to provide an economical, simple process for the production of 3,3-dimethyl-2-oxo-butyric acid from readily available materials.

This object is realized in accordance with the present invention pursuant to which 3,3-dimethyl-2-oxo-butyric acid is produced by introducing chlorine into pinacolone in two stages under different conditions of temperature to produce substantially pure dichloropinacolone, adding the dichloropinacolone to an aqueous solution containing more than three times its molar amount of an alkali at a temperature of at least about 50° C, thereby to produce 3,3-dimethyl-2-hydroxy-butyric acid salt, and contacting said solution at a pH of about 9 to 12 and a temperature of about 50° to 60° C with approximately the stoichiometric amount of a permanganate, thereby to produce a substantially pure solution of a salt of 3,3-dimethyl-2-oxo-butyric acid.

The reactions described hereinabove are as follows:

The chlorine is introduced at a temperature from about 20° to 55° C with the initial introduction taking place at about 20° to 40° C, especially about 20° to 30° C. About 60 to 80% of the total chlorine is introduced while measures are taken to cool the material and keep the temperature below about 50° C. Thereafter, in the same or a different vessel, chlorine introduction is continued with the temperature initially at least about 40° C and ultimately at least about 50° C. This is needed because dichloropinacolone melts at about 47° C and it must therefore be kept molten to permit the reaction to proceed to completion in a reasonably short time, the reaction being substantially stoichiometric. HCl gas is formed as a by-product and is absorbed in conventional manner.

The molten dichloropinacolone is then added incrementally, with agitation, to an aqueous solution containing more than three times the molar amount of alkali, e.g. sodium or potassium hydroxide of about 10 to 25% concentration by weight. The temperture of the alkali must be at least sufficient for the molten dichloropinacolone not to solidify since the solids would plug up the piping system of the recirculation. On the other hand, the temperature should not be so high that substantial amounts of dichloropinacolone are lost by sublimation. A temperature of about 50° to 55° C is especially desirable, cooling being employed to maintain the temperature. The product of the hydrolysis is an alkaline solution of 3,3-dimethyl-2-hydroxy-butyric acid, i.e. an aqueous solution of a salt of the acid.

This solution is adjusted to a pH of about 9 to 12, especially about 9 to 10 for best yields, and to it there is added an alkali metal permanganate, e.g. potassium permanganate. The solution is desirably maintained at a

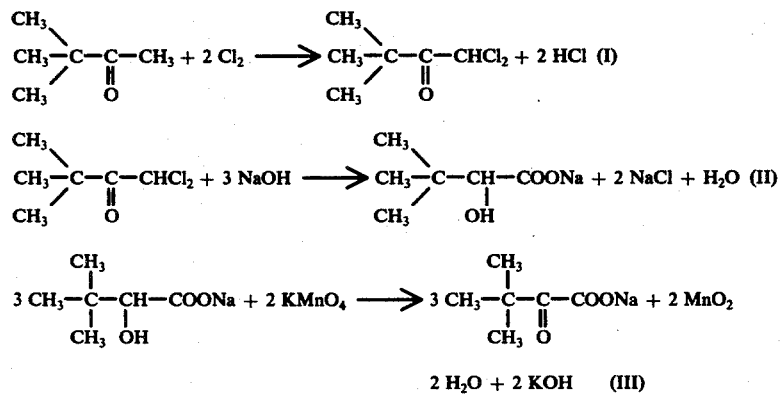

The individual process steps are interrelated in that it is the high purity of the dichloropinacolone which permits the practical permanganate oxidation to high purity 3,3-dimethyl-2-oxo-butyric acid, i.e. with dichloropinacolone of less than about 97% purity the manganese dioxide which forms upon ultimate oxidation is extremely fine and cannot readily be separated either by filtration or centrifugation.

Turning now to the individual steps, the chlorination of pinacolone is preferably carried out without a solvent. Organic solvents serve no purpose since they are not required and therefore add unnecessarily to the cost of the process. Water would merely react with the chlorine and form hypochlorite which would produce undesirable side reactions so it is preferably present in no more than the limit of its solubility in pinacolone, i.e. about 2%.

temperature of about 50° to 60° C during the addition, lower temperatures requiring extremely long reaction times and higher temperatures lowering the yield due to the activity of the permanganate. For this same reason the permanganate is desirably added incrementally over a period of several hours to control the oxidation.

The reaction is exothermic and to dissipate the heat the solution is desirably caused to boil, the vapors being condensed and recycled. To effect boiling at a maximum temperature well below 100° C obviously it is necessary to employ a vacuum.

The reaction mixture is highly corrosive so it is desirable the reaction vessel has an inert lining, e.g. brick, glass, or the like.

The permanganate is usually added as a solid and immediately dissolves but, as oxidation proceeds, it is reduced to manganese dioxide which precipitates out.

Actually, the solid product is a hydrate thereof containing alkali but will, for convenience, be identified as manganese dioxide per se. If the initially obtained dichloropinacolone was of high purity the manganese dioxide will be black and of coarse, crystalline structure which lends itself to ready separation from the solution of desired material by centrifugation and/or filtration. If the purity of the dichloropinacolone was initially less than about 97% the precipitated manganese dioxide will be brown and extremely fine in structure. This will resist separation by centrifugation and, if filtration is employed, it will rapidly plug the filter so separation cannot proceed.

As noted hereinabove, the temperture during permanganate addition is also important to the process and, if less than about 50° C at the very outset of addition, the manganese dioxide then produced will be of undesirably fine structure.

After separation of the manganese dioxide there is left a solution of substantially pure salt of 3,3-dimethyl-2-oxo-butyric acid and this can be employed directly in condensation with thiocarbohydrazide as described hereinabove or it can be isolated as such or as the free acid and kept for later reaction.

The invention will be further described in the following illustrative example wherein parts are by weight unless otherwise expressed.

EXAMPLE a. Two thousand gallons (13,320 pounds) of pinacolone are charged to a 3,000 gallon glass-lined reactor, equipped with agitator, condenser, dip pipe and jacket. At a temperature between 20° C and 30° C, the addition of 12,824 pounds (70% of total) of gaseous chlorine is started at a rate of approximately 1,200 pounds per hour. The reaction mixture is stirred during chlorine addition. The temperature is kept at 25°-35° C by cooling with brine. The chlorine is introduced through a dip pipe under the surface of the liquid. After addition of 12,000 pounds of chlorine the temperature is allowed to rise to a maximum of 40° C. HCl which is evolved is cooled by a condenser supplied with brine in order to minimize losses of pinacolone carried out with HCl. The batch is then transferred to a second reactor of the same size and type as the first reactor.

5,500 pounds of gaseous chlorine is added over a period of about eight hours at temperature rising continously from 40° C to 55° C. Initially, the reaction mixture is cooled with water. At the end of the reaction, the temperature is maintained by applying 60° C warm water to the reactor jacket in order to prevent dichloropinacolone from solidifying. HCl evolved is absorbed in the HCl absorption system. The course of the reaction is monitored by subjecting samples to gas chromatographic analysis and chlorine introducition discontinued upon introduction of the stoichiometric amount. The melts at 46°-47° C and is obtained in substantially quantitive yield at 22,000 pounds. It analyzes 97-98% dichloropinacolone, < 0.5% monochloropinacooone, < 0.5% trichloropinacolone and < 0.1% of pinacolone.

b. 25,000 pounds (3,000 gallons) of water are charged to a 5,300 gallon reactor. The reactor is carbon steel, rubber-lined and brick-lined, and equipped with agitator and baffles. 11,750 pounds (918 gallons) of 50% caustic are added. The reaction mixture is heated to 55° C by circulating it through an outside heat exchanger heated with steam. 7,720 pounds (835 gallons) of dichloropinacolone from (a) are added over a period of five hours. The dichloropinacolone is added as a liquid having a temperature of 50°-55° C. The reaction temperature is kept at 50°-55° C by circulating the rection mixture through outside heat exchangers cooled with 5° C water. After the addition of dichloropinacolone is completed, the reaction mixture is stirred for one hour at 50°-55° C. Then the pH is adjusted from 14 to 9 by the addition of concentrated sulfuric acid. There are obtained 44,800 pounds (4,520 gallons) of solution of the sodium salt of 3,3-dimethyl-2-hydroxy butyric acid, containing 5,685 pounds of 3,3-dimethyl-2-hydroxy butyric acid (100%). the yield based on dichloropinacolone is 98% of the theory.

C. 39,640 pounds (4,000 gallons) of a solution of the sodium salt of 3,3-dimethyl-2-hydroxy butyric acid containing 5,030 pounds (100%) of 3,3-dimethyl-2-hydroxy butyric acid obtained in (b), are charged to a 5,030 gallon carbon steel rubber-lined and brick-lined reactor. Under stirring, the solution, which has a pH of 9, is heated up to 53° C with direct steam. The reactor is evacuated to an absolute pressure of 80 millibars. After commencement of boiling and reflux of the condensate, condensed in shell and tube heat exchanger cooled with 20°-30° C cooling water, the addition of 4,820 pounds potassium permanganate crystals is started. To prevent foaming 2 gallons of anti-foam are added. The permanganate is added through a rotary valve over a period of five hours at such a rate that constant controlled reflux is maintained. When the addition of potassium permanganate is completed, no more heat of reaction is observed. The reactor is vented and the batch transferred to a 6,000 gallon steel rubber-lined after-oxidation reactor. The warm reaction mixure is then pumped to a centrifuge where the aqueous solution is separated from the MnO$_2$ resulting from the reduction of KMnO$_4$. Yield: 2,650 pounds MnO$_2$ (100%) or 5,300 pounds of wet cake. The yield of desired reaction product is a solution of 44,566 pounds (4,643 gallons) of sodium salt of 3,3-dimethyl-2-oxo-butyric acid containing 4,457 pounds of oxo acid (100%).

d. In some runs a large excess of KMnO$_4$ may be detected, in which event the requisite amount of additional sodium salt of 3,3-dimethyl-2-hydroxy-butyric acid is added at 50°-55° C until all of the KMnO$_4$ has reacted, and then decolorization is effected. In other runs if the analysis indicates an excess of hydroxy acid, further KMnO$_4$ is added in small increments until the excess hydroxy acid is consumed.

It will be appreciated that the instant specification and examples are set forth by way of illustration and not limitation, and that various modifications and changes may be made without departing from the spirit and scope of the present invention.

What is claimed is:

1. A process comprising introducing into pinacolone twice the molar amount of chlorine, the exothermic reaction mass being cooled initially to maintain the temperature below about 50° C until about 60 to 80% of the chlorine has been introduced, then heating the reaction mass during introducing of the remainder of the chlorine, with the temperature being raised during heating to a final temperature above 50° C, the temperature being kept high enough to maintain the mass in liquid state, thereby to produce dichloropinacolone, and terminating chlorine introduction when the dichloropinacolone content of the reaction mass is at least about 97%.

2. The process of claim 1, wherein the temperature during addition of about the first 60 to 80% of the chlorine is about 20° to 30° C, is thereafter permitted to rise to at least about 40° C when commencing addition of the balance and at the end of addition of the balance is at about 50° to 55° C.

* * * * *